US012291564B2

(12) United States Patent
Cui et al.

(10) Patent No.: US 12,291,564 B2
(45) Date of Patent: May 6, 2025

(54) BINDING PROTEIN OF NS1 PROTEIN

(71) Applicant: FAPON BIOTECH INC., Shenzhen (CN)

(72) Inventors: Peng Cui, Dongguan (CN); Zhiqiang He, Dongguan (CN); Yuan Meng, Dongguan (CN); Dongmei Zhong, Dongguan (CN)

(73) Assignee: FAPON BIOTECH INC., Guangdong (CN)

( * ) Notice: Subject to any disclaimer, the term of this patent is extended or adjusted under 35 U.S.C. 154(b) by 151 days.

(21) Appl. No.: 17/270,341

(22) PCT Filed: Aug. 26, 2019

(86) PCT No.: PCT/CN2019/102630
§ 371 (c)(1),
(2) Date: Apr. 8, 2024

(87) PCT Pub. No.: WO2020/043067
PCT Pub. Date: Mar. 5, 2020

(65) Prior Publication Data

US 2021/0324054 A1 Oct. 21, 2021

(30) Foreign Application Priority Data

Aug. 28, 2018 (CN) ........................ 201811001557.1

(51) Int. Cl.
*C07K 16/10* (2006.01)
*G01N 33/569* (2006.01)

(52) U.S. Cl.
CPC ... *C07K 16/1081* (2013.01); *G01N 33/56983* (2013.01); *C07K 2317/565* (2013.01); *C07K 2317/567* (2013.01); *C07K 2317/92* (2013.01); *G01N 2333/185* (2013.01)

(58) Field of Classification Search
CPC .......... C07K 16/1081; C07K 2317/565; C07K 2317/567; C07K 2317/92; C07K 2317/94; G01N 33/56983; G01N 2333/185; G01N 2469/10; G01N 33/68; Y02A 50/30
See application file for complete search history.

(56) References Cited

U.S. PATENT DOCUMENTS

| | | |
|---|---|---|
| 2013/0164734 A1 | 6/2013 | Raychaudhuri et al. |
| 2017/0233460 A1 | 8/2017 | Bosch et al. |

FOREIGN PATENT DOCUMENTS

| | | | |
|---|---|---|---|
| CN | 104768574 A | 7/2015 |
| CN | 109053883 A | 12/2018 |
| WO | 2017223286 A1 | 12/2017 |

OTHER PUBLICATIONS

Dondelinger M, et. al. Front Immunol. Oct. 16, 2018;9:2278. (Year: 2018).*
Endale A, et. al. Infect Drug Resist. Oct. 19, 2021;14:4291-4299. (Year: 2021).*
Saxena AK. Chain L, Fab fragment of antibody 2A8, Light chain. PDB: 3S62_L. Dep Apr. 4, 2012. (Year: 2012).*
Bowie JU, et. al. Science. Mar. 16, 1990;247(4948):1306-10. (Year: 1990).*
Winkler K, et. al. J Immunol. Oct. 15, 2000;165(8):4505-14. (Year: 2000).*
Kussie PH, et. al. J Immunol. Jan. 1, 1994;152(1):146-52. (Year: 1994).*
Chen Z, et. al. Nat Commun. Mar. 30, 2015;6:6714. (Year: 2015).*
Sela-Culang I, et. al. Front Immunol. Oct. 8, 2013;4:302. (Year: 2013).*
Sirin S, et. al. Protein Sci. Feb. 2016;25(2):393-409. Epub Nov. 6, 2015. (Year: 2015).*
Tsuchiya Y, et. al. Protein Sci. Apr. 2016;25(4):815-25. Epub Jan. 20, 2016. (Year: 2016).*
Collis AV, et. al. J Mol Biol. Jan. 10, 2003;325(2):337-54. (Year: 2003).*
Qiang Fu et al., "Prokaryotic Expression of NS1 Protein of Dengue Virus and Application in Rapid Diagnosis of Dengue Fever," Journal of Sun Yat-Sen University (Medical Sciences), vol. 33, No. 3, May 2012, pp. 316-321.
First Office Action with English translation mailed on Aug. 16, 2021 for corresponding Chinese Application No. 201811001557.1.
Gao, Hongli et al., "The Preparation and Preliminary Application of the Group-specific Monoclonal Antibodies Against the Nonstructural Glycoprotein 1 of Dengue Virus", Journal of Tropical Medicine, vol. 11, No. 6, Jun. 30, 2011, pp. 620-623 and 646.
International Search Report for corresponding application No. PCT/CN2019/102630 mailed Nov. 26, 2019.
Office Action with English translation for corresponding Korean Application No. 10-2021-7005244 issued on Apr. 20, 2023.
Kebaneilwe Lebani et al., "Isolation of serotype-specific antibodies against dengue virus non-structural protein 1 using phage display and application in a multiplexed serotyping assay", PloS One 12(7): e0180669, https://doi.org/10.1371/journal.pone.0180669, Jul. 6, 2017, pp. 1-18.
Lee instar., "The field rapid diagnosis kit development about the dengue (heat) virus NS1 antigen", Small and Medium Industry Administration first step business of technology development final report (Apr. 2014).

* cited by examiner

*Primary Examiner* — Rachel B Gill

(57) ABSTRACT

Provided is an isolated binding protein including an antigen-binding domain that binds to NS1 protein. The isolated binding protein includes specific heavy chain CDRs and light chain CDRs. The binding protein can specifically recognize and bind to NS1, and has relatively high sensitivity and specificity, thereby achieving the detection of dengue virus. Moreover, the binding protein is not required to be produced by inducing hybridoma cells in mouse abdominal cavity, and thus it is simple in production and has more stable antibody function.

17 Claims, No Drawings

Specification includes a Sequence Listing.

SEQUENCE LISTING

```
<160> NUMBER OF SEQ ID NOS: 28

<210> SEQ ID NO 1
<211> LENGTH: 23
<212> TYPE: PRT
<213> ORGANISM: Artificial Sequence
<220> FEATURE:
<223> OTHER INFORMATION: Light chain framework region FR-L1

<400> SEQUENCE: 1

Gln Ile Val Leu Thr Gln Ser Pro Ala Ile Met Ser Ala Ser Pro Gly
1               5                   10                  15

Glu Lys Val Thr Met Thr Cys
            20


<210> SEQ ID NO 2
<211> LENGTH: 15
<212> TYPE: PRT
<213> ORGANISM: Artificial Sequence
<220> FEATURE:
<223> OTHER INFORMATION: Light chain framework region FR-L2
<220> FEATURE:
<221> NAME/KEY: MISC_FEATURE
<223> OTHER INFORMATION: Light chain framework region FR-L2

<400> SEQUENCE: 2

Trp Tyr Gln Gln Lys Ser Gly Thr Ser Pro Lys Arg Trp Ile Tyr
1               5                   10                  15


<210> SEQ ID NO 3
<211> LENGTH: 30
<212> TYPE: PRT
<213> ORGANISM: Artificial Sequence
<220> FEATURE:
<223> OTHER INFORMATION: Light chain framework region FR-L3

<400> SEQUENCE: 3

Pro Val Arg Phe Ser Gly Ser Gly Ser Gly Thr Ser Tyr Ser Leu Thr
1               5                   10                  15

Ile Ser Ser Met Glu Ala Glu Asp Ala Ala Thr Tyr Phe Cys
            20                  25                  30


<210> SEQ ID NO 4
<211> LENGTH: 10
<212> TYPE: PRT
<213> ORGANISM: Artificial Sequence
<220> FEATURE:
<223> OTHER INFORMATION: Light chain framework region FR-L4

<400> SEQUENCE: 4

Phe Gly Ala Gly Thr Lys Leu Glu Leu Lys
1               5                   10


<210> SEQ ID NO 5
<211> LENGTH: 25
<212> TYPE: PRT
<213> ORGANISM: Artificial Sequence
<220> FEATURE:
<223> OTHER INFORMATION: Heavy chain framework region FR-H1

<400> SEQUENCE: 5
```

-continued

```
Glu Val Gln Leu Gln Gln Pro Gly Pro Glu Leu Val Lys Pro Gly Ala
1               5                   10                  15

Ser Val Lys Met Ser Cys Lys Ala Ser
            20                  25


<210> SEQ ID NO 6
<211> LENGTH: 14
<212> TYPE: PRT
<213> ORGANISM: Artificial Sequence
<220> FEATURE:
<223> OTHER INFORMATION: Heavy chain framework region FR-H2

<400> SEQUENCE: 6

Trp Val Arg Gln Lys Pro Gly Gln Gly Leu Glu Trp Ile Gly
1               5                   10


<210> SEQ ID NO 7
<211> LENGTH: 30
<212> TYPE: PRT
<213> ORGANISM: Artificial Sequence
<220> FEATURE:
<223> OTHER INFORMATION: Heavy chain framework region FR-H3

<400> SEQUENCE: 7

Lys Ala Ile Leu Thr Ser Asp Lys Ser Ser Ser Thr Ala Tyr Met Gln
1               5                   10                  15

Leu Ser Ser Leu Thr Ser Glu Asp Ser Ala Val Tyr Tyr Cys
            20                  25                  30


<210> SEQ ID NO 8
<211> LENGTH: 11
<212> TYPE: PRT
<213> ORGANISM: Artificial Sequence
<220> FEATURE:
<223> OTHER INFORMATION: Heavy chain framework region FR-H4
<220> FEATURE:
<221> NAME/KEY: MISC_FEATURE
<223> OTHER INFORMATION: Heavy chain framework region FR-H4

<400> SEQUENCE: 8

Trp Gly Gln Gly Thr Ser Val Thr Val Ser Ser
1               5                   10


<210> SEQ ID NO 9
<211> LENGTH: 107
<212> TYPE: PRT
<213> ORGANISM: Artificial Sequence
<220> FEATURE:
<223> OTHER INFORMATION: Light chain constant region

<400> SEQUENCE: 9

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95
```

-continued

```
Pro Ile Val Lys Ser Phe Asn Arg Asn Glu Cys
            100                 105


<210> SEQ ID NO 10
<211> LENGTH: 324
<212> TYPE: PRT
<213> ORGANISM: Artificial Sequence
<220> FEATURE:
<223> OTHER INFORMATION: Heavy chain constant region

<400> SEQUENCE: 10

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Lys Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys


<210> SEQ ID NO 11
<211> LENGTH: 213
<212> TYPE: PRT
```

<213> ORGANISM: Artificial Sequence
<220> FEATURE:
<223> OTHER INFORMATION: Light chain

<400> SEQUENCE: 11

```
Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Ile Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Pro Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Phe Cys Gln Tyr Trp Arg Ser Asp Leu Pro Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 12
<211> LENGTH: 442
<212> TYPE: PRT
<213> ORGANISM: Artificial Sequence
<220> FEATURE:
<223> OTHER INFORMATION: Heavy chain

<400> SEQUENCE: 12

```
Glu Val Gln Leu Gln Gln Pro Gly Pro Glu Leu Val Lys Pro Gly Ala
1               5                   10                  15

Ser Val Lys Met Ser Cys Lys Ala Ser Gly Tyr Thr Val Thr Ser Tyr
            20                  25                  30

Val Ile His Trp Val Arg Gln Lys Pro Gly Gln Gly Leu Glu Trp Ile
        35                  40                  45

Gly Tyr Met Asn Ala Tyr Asn Asp Gly Ile Lys Tyr Asn Glu Lys Phe
    50                  55                  60

Ile Gly Lys Ala Ile Leu Thr Ser Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Lys Glu Gly Leu Phe Tyr Val Met Asp Tyr Trp Gly Gln Gly Thr
            100                 105                 110
```

-continued

```
Ser Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Gln Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Lys Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440
```

<210> SEQ ID NO 13
<211> LENGTH: 10
<212> TYPE: PRT
<213> ORGANISM: Artificial Sequence
<220> FEATURE:
<223> OTHER INFORMATION: CDR-VH1
<220> FEATURE:
<221> NAME/KEY: MISC_FEATURE
<222> LOCATION: (4)..(4)
<223> OTHER INFORMATION: Xaa is V or F
<220> FEATURE:
<221> NAME/KEY: MISC_FEATURE
<222> LOCATION: (7)..(7)
<223> OTHER INFORMATION: Xaa is T, S or Y

<400> SEQUENCE: 13

Gly Tyr Thr Xaa Thr Ser Xaa Val Ile His
1 5 10

<210> SEQ ID NO 14
<211> LENGTH: 17
<212> TYPE: PRT
<213> ORGANISM: Artificial Sequence
<220> FEATURE:
<223> OTHER INFORMATION: CDR-VH2
<220> FEATURE:
<221> NAME/KEY: MISC_FEATURE
<222> LOCATION: (4)..(4)
<223> OTHER INFORMATION: Xaa is A, P or G
<220> FEATURE:
<221> NAME/KEY: MISC_FEATURE
<222> LOCATION: (9)..(9)
<223> OTHER INFORMATION: Xaa is L or I
<220> FEATURE:
<221> NAME/KEY: MISC_FEATURE
<222> LOCATION: (13)..(13)
<223> OTHER INFORMATION: Xaa is E, D or N

<400> SEQUENCE: 14

Tyr Met Asn Xaa Tyr Asn Asp Gly Xaa Lys Tyr Asn Xaa Lys Phe Ile
1 5 10 15

Gly

<210> SEQ ID NO 15
<211> LENGTH: 11
<212> TYPE: PRT
<213> ORGANISM: Artificial Sequence
<220> FEATURE:
<223> OTHER INFORMATION: CDR-VH3
<220> FEATURE:
<221> NAME/KEY: MISC_FEATURE
<222> LOCATION: (2)..(2)
<223> OTHER INFORMATION: Xaa is K or R
<220> FEATURE:
<221> NAME/KEY: MISC_FEATURE
<222> LOCATION: (9)..(9)
<223> OTHER INFORMATION: Xaa is M or F

<400> SEQUENCE: 15

Thr Xaa Glu Gly Leu Phe Tyr Val Xaa Asp Tyr
1 5 10

<210> SEQ ID NO 16
<211> LENGTH: 10
<212> TYPE: PRT
<213> ORGANISM: Artificial Sequence
<220> FEATURE:
<223> OTHER INFORMATION: CDR-VL1
<220> FEATURE:
<221> NAME/KEY: MISC_FEATURE
<222> LOCATION: (2)..(2)
<223> OTHER INFORMATION: Xaa is G or A
<220> FEATURE:
<221> NAME/KEY: MISC_FEATURE
<222> LOCATION: (6)..(6)
<223> OTHER INFORMATION: Xaa is I, L or V

<400> SEQUENCE: 16

Ser Xaa Thr Ser Ser Xaa Ser Tyr Met His
1 5 10

<210> SEQ ID NO 17
<211> LENGTH: 9
<212> TYPE: PRT
<213> ORGANISM: Artificial Sequence
<220> FEATURE:
<223> OTHER INFORMATION: CDR-VL2
<220> FEATURE:
<221> NAME/KEY: MISC_FEATURE
<222> LOCATION: (2)..(2)
<223> OTHER INFORMATION: Xaa is T or S
<220> FEATURE:
<221> NAME/KEY: MISC_FEATURE
<222> LOCATION: (8)..(8)
<223> OTHER INFORMATION: Xaa is P, A or G

<400> SEQUENCE: 17

Asp Xaa Ser Lys Leu Ala Ser Xaa Val
1 5

<210> SEQ ID NO 18
<211> LENGTH: 9
<212> TYPE: PRT
<213> ORGANISM: Artificial Sequence
<220> FEATURE:
<223> OTHER INFORMATION: CDR-VL3
<220> FEATURE:
<221> NAME/KEY: MISC_FEATURE
<222> LOCATION: (2)..(2)
<223> OTHER INFORMATION: Xaa is Q, Y or W
<220> FEATURE:
<221> NAME/KEY: MISC_FEATURE
<222> LOCATION: (6)..(6)
<223> OTHER INFORMATION: Xaa is D or V

<400> SEQUENCE: 18

Gln Xaa Trp Arg Ser Xaa Leu Pro Thr
1 5

<210> SEQ ID NO 19
<211> LENGTH: 30
<212> TYPE: DNA
<213> ORGANISM: Artificial Sequence
<220> FEATURE:
<223> OTHER INFORMATION: SMARTER II A oligonucleotide
<220> FEATURE:
<221> NAME/KEY: misc_feature
<222> LOCATION: (26)..(30)
<223> OTHER INFORMATION: n is a, c, g, or t

<400> SEQUENCE: 19
aagcagtggt atcaacgcag agtacnnnnn 30

<210> SEQ ID NO 20
<211> LENGTH: 27
<212> TYPE: DNA
<213> ORGANISM: Artificial Sequence
<220> FEATURE:
<223> OTHER INFORMATION: 5'-RACE CDS primer
<220> FEATURE:
<221> NAME/KEY: misc_feature
<222> LOCATION: (26)..(27)
<223> OTHER INFORMATION: N=A, C, G or T, V=A, G, or C

<400> SEQUENCE: 20
tttttttttt tttttttttt tttttvn 27

<210> SEQ ID NO 21
<211> LENGTH: 45
<212> TYPE: DNA
<213> ORGANISM: Artificial Sequence
<220> FEATURE:
<223> OTHER INFORMATION: Universal Primer A Mixture (UPM)

<400> SEQUENCE: 21

-continued ctaatacgac tcactatagg gcaagcagtg gtatcaacgc agagt 45

<210> SEQ ID NO 22
<211> LENGTH: 23
<212> TYPE: DNA
<213> ORGANISM: Artificial Sequence
<220> FEATURE:
<223> OTHER INFORMATION: Nested Universal Primer A (NUP)

<400> SEQUENCE: 22
aagcagtggt atcaacgcag agt 23

<210> SEQ ID NO 23
<211> LENGTH: 23
<212> TYPE: DNA
<213> ORGANISM: Artificial Sequence
<220> FEATURE:
<223> OTHER INFORMATION: mkR

<400> SEQUENCE: 23
ctaacactca ttcctgttga agc 23

<210> SEQ ID NO 24
<211> LENGTH: 23
<212> TYPE: DNA
<213> ORGANISM: Artificial Sequence
<220> FEATURE:
<223> OTHER INFORMATION: mHR

<400> SEQUENCE: 24
tcatttacca ggagagtggg aga 23

<210> SEQ ID NO 25
<211> LENGTH: 34
<212> TYPE: DNA
<213> ORGANISM: Artificial Sequence
<220> FEATURE:
<223> OTHER INFORMATION: DN7F8-HF

<400> SEQUENCE: 25
cagaagctta tgaagttgcc tgttaggctg ttgg 34

<210> SEQ ID NO 26
<211> LENGTH: 39
<212> TYPE: DNA
<213> ORGANISM: Artificial Sequence
<220> FEATURE:
<223> OTHER INFORMATION: DN7F8-HR

<400> SEQUENCE: 26
caggaattct tatcatttac caggagagtg ggagaggct 39

<210> SEQ ID NO 27
<211> LENGTH: 35
<212> TYPE: DNA
<213> ORGANISM: Artificial Sequence
<220> FEATURE:
<223> OTHER INFORMATION: DN7F8-LF

<400> SEQUENCE: 27
cataagctta tgaagttgcc tgttaggctg ttggt 35

<210> SEQ ID NO 28
<211> LENGTH: 40
<212> TYPE: DNA
<213> ORGANISM: Artificial Sequence -continued

```
<220> FEATURE:
<223> OTHER INFORMATION: DN7F8-LR

<400> SEQUENCE: 28

atcgaattct tactaacact cattcctgtt gaagctcttg                              40
```

BINDING PROTEIN OF NS1 PROTEIN

CROSS-REFERENCE TO RELATED APPLICATIONS

The present application is a national stage of International Application No. PCT/CN2019/102630, filed on Aug. 26, 2019, which claims a priority to Chinese Patent Application No. 201811001557.1, titled "Binding Protein of NS1 Protein", filed on Aug. 28, 2018 in the China Patent Office, with the content of which is incorporated herein by reference in its entirety.

TECHNICAL FIELD

The present disclosure relates to the fields of biotechnology and medical technology, and particularly, to a binding protein of NS1 protein.

BACKGROUND

Dengue fever (DF) is an acute mosquito-borne infectious disease caused by 4 serotype viruses (DENV-1, DENV-2, DENV-3, and DENV-4), mainly transmitted by *Aedes aegypti* and *Aedes albopictus*. DF is an arboviral disease with the most widespread distribution, the most incidence, and more harm. It is widely prevalent in more than 100 countries and regions in tropical, subtropical Africa, the Americas, Southeast Asia, and the Western Pacific.

Clinically, DF is a severe flu-like disease. The main manifestations include sudden onset, high fever, severe headache, posterior orbital pain, muscle and joint pain, which may be accompanied by skin rash, lymphadenopathy, and leukopenia, which may affect all people, with the symptoms varying depending on the age of the patient. Such a type of disease is generally referred as to the classical dengue fever, which spreads rapidly and can cause a large-scale epidemic. During the epidemic of dengue fever, a prevalence rate of susceptible people is generally 40%-50%, or as high as 80%-90%, but a case fatality rate thereof is very low. Dengue hemorrhagic fever is characterized by high fever, hemorrhage, hepatomegaly, and circulatory failure in severe cases, with a high case fatality rate, and it is a more serious clinical type. The accompanied shock syndrome is called dengue shock syndrome.

No specific treatment for dengue fever is available. If there is no proper treatment, the case fatality rate of dengue hemorrhagic fever may exceed 20%, and with effective supportive therapy, the case fatality rate can be lower than 1%. The essentials of diagnosis of dengue fever include: 1) epidemiological data, activities in the 15 days before the onset, visiting the endemic areas or not, and experience of mosquito bites; 2) clinical features, sudden onset, fever, "three pains and three reds", skin rash; and 3) laboratory tests, decreases in white blood cells and platelets; detected serum characteristics are positive for IgM; IgG in recovery phase increases 4 times compared to that in the acute phase; virus or specific antigen are isolated. Clinical methods for detecting dengue virus include virus culture, serological detection, and viral nucleic acid detection, etc. Virus isolation takes a long time and cannot achieve the purpose of rapid diagnosis, and conventional serological diagnosis may be disturbed by the existence of extensive cross-reactions. Colloidal gold-labeled immunochromatographic methods, due to the characteristics of speediness, convenience, no need for special equipment, on-site detection, have become the research hotspot in the rapid diagnosis of infectious diseases. NS1 protein is the only glycoprotein among the non-structural proteins of dengue virus. It has strong antigenicity and does not trigger antibody-dependent enhanced infection (ADE), and thus it can be used as a target for colloidal gold detection. The colloidal gold detection requires a specific monoclonal antibody against NS1 protein, and traditionally, mouse-derived monoclonal antibodies have been used in clinical practice. For a long time, murine monoclonal antibodies have been widely used in scientific research, clinical diagnosis and treatment. However, the production of hybridomas requires the use of mouse abdominal cavity to produce hybridomas, which is particularly affected by the individual mice, such that the production is unstable, batch-to-batch difference is great, and purification is difficult due to the inclusion of mouse autoantibodies.

SUMMARY

The present disclosure is based on the obtained anti-dengue virus NS1 7F8 monoclonal antibody. Through cloning, identification and analysis of the genetic structure, the CDR region sequence thereof is determined, a corresponding isolated binding protein including an antigen-binding domain that binds to NS1 protein is constructed, and a corresponding eukaryotic cell expression system is established, producing and purifying the binding protein.

The present disclosure provides an isolated binding protein including an antigen-binding domain that binds to NS1 protein. The antigen-binding domain includes at least one complementary determining region selected from the following amino acid sequences, or the antigen-binding domain has at least 80% sequence identity with the complementary determining regions of the following amino acid sequences and has an affinity for the NS1 protein of $KD \leq 5.78\times10^{-8}$ mo/L:

- a complementary determining region CDR1-VH of G-Y-T-X1-T-S-X2-V-I-H, where X1 is V or F, and X2 is T, S or Y (SEQ ID NO: 13);
- a complementary determining region CDR2-VH of Y-M-N-X1-Y-N-D-G-X2-K-Y-N-X3-K-F-I-G, where X1 is A, P or G, X2 is L or I, and X3 is E, D or N (SE Q ID NO: 14);
- a complementary determining region CDR3-VH of T-X1-E-G-L-F-Y-V-X2-D-Y, where X1 is K or R, and X2 is M or F (SEQ ID NO: 15);
- a complementary determining region CDR1-VL of S-X1-T-S-S-X2-S-Y-M-H, where X1 is G or A, and X2 is I, L or V (SEQ ID NO: 16);
- a complementary determining region CDR2-VL of D-X1-S-K-L-A-S-X2-V, where X1 is T or S, and X2 is P, A or G (SEQ ID NO: 17); and
- a complementary determining region CDR3-VL of Q-X1-W-R-S-X2-L-P-T, where X1 is Q, Y or W, and X2 is D or V (SEQ ID NO: 18).

For example, in the complementary determining region CDR1-VH, X1 is F; in the complementary determining region CDR2-VH, X1 is P, and X3 is E; in the complementary determining region CDR1-VL, X1 is A; in the complementary determining region CDR2-VL, X2 is G; and in the complementary determining region CDR3-VL, X2 is D.

For example, in the complementary determining region CDR1-VH, X2 is T.

For example, in the complementary determining region CDR1-VH, X2 is S.

For example, in the complementary determining region CDR1-VH, X2 is Y.

For example, in the complementary determining region CDR2-VH, X2 is L.

For example, in the complementary determining region CDR2-VH, X2 is I.

For example, in the complementary determining region CDR3-VH, X1 is K, and X2 is M.

For example, in the complementary determining region CDR3-VH, X1 is K, and X2 is F.

For example, in the complementary determining region CDR3-VH, X1 is R, and X2 is M.

For example, in the complementary determining region CDR3-VH, X1 is R, and X2 is F.

For example, in the complementary determining region CDR1-VH, X2 is I.

For example, in the complementary determining region CDR1-VH, X2 is L.

For example, in the complementary determining region CDR1-VH, X2 is V.

For example, in the complementary determining region CDR2-VH, X1 is T.

For example, in the complementary determining region CDR2-VH, X1 is S.

For example, in the complementary determining region CDR3-VL, X1 is Q.

For example, in the complementary determining region CDR3-VL, X1 is Y.

For example, in the complementary determining region CDR3-VL, X1 is W.

In one or more embodiments, an amino acid at a corresponding site of the complementary determining region is as follows:

| Site | CDR-VH1 X2 | CDR-VH2 X2 | CDR-VH3 X1/X2 | CDR-VL1 X2 | CDR-VL2 X1 | CDR-VL3 X1 |
|---|---|---|---|---|---|---|
| Mutation 1 | T | L | K/M | I | T | Q |
| Mutation 1-1 | S | I | K/F | L | S | W |
| Mutation 1-2 | Y | L | R/M | V | T | Q |
| Mutation 1-3 | T | I | R/F | I | S | Y |
| Mutation 1-4 | S | L | K/M | L | T | W |
| Mutation 1-5 | Y | I | R/F | V | S | Q |
| Mutation 1-6 | T | I | K/M | I | T | Y |
| Mutation 1-7 | S | L | K/F | L | S | W |
| Mutation 1-8 | Y | I | R/M | V | T | Q |
| Mutation 1-9 | T | L | R/F | I | S | Y |
| Mutation 1-10 | S | I | K/M | L | T | W |
| Mutation 1-11 | Y | L | K/F | V | S | Q |
| Mutation 1-12 | T | I | R/M | I | T | Y |
| Mutation 1-13 | S | L | R/F | L | S | W |
| Mutation 1-14 | Y | I | K/M | V | S | Q |
| Mutation 1-15 | T | I | K/F | I | S | Y |
| Mutation 1-16 | S | L | R/M | L | T | W |
| Mutation 1-17 | Y | I | K/M | V | S | W |
| Mutation 1-18 | T | L | K/F | L | S | Y |
| Mutation 1-19 | S | I | R/M | V | T | Q |
| Mutation 1-20 | Y | L | K/F | I | S | Y |
| Mutation 1-21 | T | I | R/M | L | T | W |
| Mutation 1-22 | S | L | R/F | V | S | W |
| Mutation 1-23 | Y | L | K/F | L | S | Q |
| Mutation 1-24 | T | I | R/M | V | T | Y |
| Mutation 1-25 | S | L | R/F | I | S | W |
| Mutation 1-26 | Y | I | R/M | L | T | W |
| Mutation 1-27 | T | L | R/F | V | S | Q |
| Mutation 1-28 | S | I | K/M | V | T | Y |
| Mutation 1-29 | Y | I | R/F | I | S | W |
| Mutation 1-30 | T | L | R/M | L | T | Y |
| Mutation 1-31 | S | I | R/F | V | S | W |
| Mutation 1-32 | Y | I | K/M | V | T | Q |
| Mutation 1-33 | T | L | R/F | I | S | W |
| Mutation 1-34 | S | I | R/F | L | T | Y |
| Mutation 1-35 | Y | L | K/M | V | S | W |
| Mutation 1-36 | T | L | R/F | L | S | Q |
| Mutation 1-37 | S | I | R/F | V | T | Y |
| Mutation 1-38 | Y | L | K/M | I | S | W |
| Mutation 1-39 | T | I | R/F | L | S | Q |
| Mutation 1-40 | S | L | K/F | V | T | Y |
| Mutation 1-41 | Y | I | R/M | I | S | W |
| Mutation 1-42 | T | I | R/F | L | T | Q |
| Mutation 1-43 | S | I | K/M | L | T | Y |
| Mutation 1-44 | Y | L | R/F | V | S | Y |
| Mutation 1-45 | T | I | K/F | L | S | W |
| Mutation 1-46 | S | L | R/M | V | T | Q |
| Mutation 1-47 | Y | I | R/F | I | S | Y |
| Mutation 1-48 | T | L | K/M | L | S | W |
| Mutation 1-49 | S | I | R/F | V | T | Q |
| Mutation 1-50 | Y | L | K/F | I | T | Y |
| Mutation 1-51 | T | L | R/M | I | S | W |
| Mutation 1-52 | S | L | K/F | L | S | Q |
| Mutation 1-53 | Y | I | R/M | V | T | Y. |

As an example, the binding protein includes at least 3 CDRs; or the binding protein includes at least 6 CDRs.

As an example, the binding protein is one of nanobody, $F(ab')_2$, Fab', Fab, Fv, scFv, a bispecific antibody, and a minimum recognition unit of an antibody.

As an example, the binding protein includes light chain framework regions VL-FR1, VL-FR2, VL-FR3, and VL-FR4 that have sequences set forth as SEQ ID NO: 1 to SEQ ID NO: 4, respectively, and/or heavy chain framework regions VH-FR1, VH-FR2, VH-FR3 and VH-FR4 that have sequences set forth as SEQ ID NO: 5 to SEQ ID NO: 8, respectively.

In one or more embodiments, the binding protein further includes an antibody constant region sequence.

As an example, the constant region sequence is a sequence of a constant region selected from any one of IgG1, IgG2, IgG3, IgG4, IgA, IgM, IgE, and IgD.

As an example, the constant region is derived from a species of cattle, horse, dairy cow, pig, sheep, goat, rat, mouse, dog, cat, rabbit, camel, donkey, deer, marten, chicken, duck, goose, turkey, cockfight, or human.

As an example, the constant region is derived from a mouse;

a light chain constant region sequence is set forth as SEQ ID NO: 9; and a heavy chain constant region sequence is set forth as SEQ ID NO: 10.

The present disclosure further provides a nucleic acid encoding the binding protein as described above.

The present disclosure further provides a vector including the nucleic acid as described above.

The present disclosure further provides a host cell including the nucleic acid as described above or the vector as described above.

The present disclosure further provides a kit including one or more of the binding protein as described above, the nucleic acid as described above, or the vector as described above.

In one or more embodiments, the kit further includes a label for labeling the binding protein.

The present disclosure further provides a method for producing the binding protein as described above. The method includes a step of preparing the nucleic acid as described above or the vector as described above.

For example, the method includes the following steps: culturing the above-described host cell in a medium, and collecting the produced binding protein from the medium or from the cultured host cell.

The present disclosure further provides a use of the binding protein as described above in a preparation of a product for detecting a dengue infection.

The present disclosure further provides a use of the binding protein described in the present disclosure for detecting a dengue infection.

The present disclosure further provides a method for detecting a dengue infection. The method includes:

A) under conditions allowing a binding reaction to occur, contacting a sample from a subject with the binding protein according to the present disclosure to perform the binding reaction; and B) detecting immune complex produced in the binding reaction, in which a presence of the immune complex indicates a presence of a dengue infection.

The isolated binding protein including an antigen-binding domain that binds to NS1 protein, provided in the present disclosure, includes specific heavy chain CDRs and light chain CDRs. The binding protein can specifically recognize and bind to the NS1 protein, and has high sensitivity and specificity, thereby achieving the detection of dengue virus. In addition, the binding protein is not required to be produced by inducing hybridoma cells in mouse abdominal cavity, and thus it is simple in production and has more stable antibody function.

DESCRIPTION OF EMBODIMENTS

Scientific and technical terms used in the present disclosure shall have the meanings that those skilled in the art commonly understand, unless otherwise defined herein. The meaning and scope of the term should be clear, and the definitions provided herein take precedence over any dictionary or foreign definitions in any potential ambiguity. In this application, the use of "or" means "and/or" unless stated otherwise. Furthermore, the terms "including", "comprising", and the like are non-limiting.

Generally, the nomenclature and techniques used in cell and tissue culture, molecular biology, immunology, microbiology, genetics, and protein and nucleic acid chemistry and hybridization described herein are those well known and commonly used in the related art. Unless otherwise indicated, the methods and techniques of the present disclosure are generally performed according to conventional methods well known in the art and as described in various general and more specific references, which are cited and discussed throughout this disclosure. Enzymatic reactions and purification techniques are carried out according to the manufacturer's protocols, or in the common manners in the related art or as described herein. Along with the nomenclatures used in analytical chemistry, synthetic organic chemistry, and medical and medicinal chemistry described herein, as well as their laboratory procedures and techniques are those well known and commonly used in the related art.

In order to facilitate the understanding of the present disclosure, selected terms are defined as below.

The term "amino acid" means a natural or non-natural carboxyl α-amino acid. The term "amino acid" as used in the present disclosure may include natural amino acids and non-natural amino acids. Natural amino acids include alanine (three-letters abbreviation: Ala, single-letter abbreviation: A), arginine (Arg, R), asparagine (Asn, N), aspartic acid (Asp, D), cysteine (Cys, c), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V). Non-natural amino acids include, but are not limited to, α-aminoadipate, aminobutyric acid, citrulline, homocitrulline, homoleucine, homoarginine, hydroxyproline, norleucine, pyridylalanine, sarcosine, etc.

The term "isolated binding protein" is a protein that, due to its derived origin or source, does not bind to a naturally-binding component that accompanies it in its natural state; a protein that is substantially free of other proteins from the same species; a protein expressed by cells from different species; or a protein not exist in nature. Thus, a protein that is chemically synthesized or synthesized in a cellular system different from the cell of its natural origin is "isolated" from its naturally associated components. The protein can also be substantially free of naturally-binding components by isolation, for example using protein purification techniques well known in the related art.

The term "isolated binding protein including an antigen-binding domain" refers broadly to all proteins/protein fragments that include a CDR region. The term "antibody" includes polyclonal and monoclonal antibodies and the antigen-compound-binding fragments of these antibodies, including Fab, F(ab')2, Fd, Fv, scFv, bispecific antibodies, and the minimum recognition units of antibodies, as well as single-chain derivatives of these antibodies and fragments. The type of antibody can be selected from IgG1, IgG2, IgG3, IgG4, IgA, IgM, IgE, or IgD. In addition, the term "antibody" includes natural antibodies, as well as non-natural antibodies, including, for example, chimeric, bifunctional, and humanized antibodies, and related synthetic isoforms. The term "antibody" is used interchangeably with "immunoglobulin".

The "variable region" or "variable domain" of an antibody refers to an amino-terminal domain of a heavy or light chain of an antibody. The variable domain of a heavy chain may be referred to as "VH". The variable domain of a light chain can be referred to as "VL". These domains are usually the most variable part of an antibody and contain an antigen binding site. The light or heavy chain variable region is composed of three hypervariable regions called "complementary determining regions" or "CDRs", and a framework region (FR) separating the hypervariable regions. The framework region of an antibody, i.e., the framework region of a combination of essential light and heavy chains, plays a role in positioning and aligning CDRs. The CDRs are primarily responsible for binding to the antigen.

As used herein, the term "bispecific antibody" or "bifunctional antibody" refers to an artificial hybrid binding protein having two different pairs of heavy/light chains and two different binding sites. The bispecific binding protein can be produced by a variety of methods, including fusion hybridomas or linking of Fab' fragments.

As used herein, the term "sequence identity" refers to the similarity between at least two different sequences. The identity percentage can be determined by standard algorithms, such as Basic Local Alignment Search Tools (BLAST); Needleman's algorithms, etc.; or Meyers's algorithm, etc. In one or more embodiments, a set of parameters may be a blocks substitution matrix (Blosum 62), and a gap penalty of 12, a gap extension penalty of 4, and a frameshift gap penalty of 5. In one or more embodiments, the identity percentage between two amino acid or nucleotide sequences can also be determined using the algorithm by Meyers and Miller ((1989) CABIOS 4:11-17), which has been incorporated into ALIGN program (version 2.0), using a PAM120 weighted residue table, gap length penalty of 12, and gap penalty of 4. The identity percentage is usually calculated by comparing the similar length of the sequences.

As used herein, the term "affinity" refers to a binding strength of an antigen-binding domain of a binding protein or antibody to an antigen or epitope. The affinity can be measured by KD value, the smaller the KD value, the greater the affinity.

The present disclosure provides an isolated binding protein, which includes an antigen-binding domain that binds to NS1 protein. The antigen-binding domain includes at least one complementary determining region selected from the following amino acid sequences, or the antigen-binding domain has at least 80% sequence identity with the complementary determining regions of the following amino acid sequences and has an affinity for the NS1 protein of KD≤$5.78\times10^{-8}$ mo/L:

- a complementary determining region CDR1-VH of G-Y-T-X1-T-S-X2-V-I-H, where X1 is V or F, and X2 is T, S or Y;
- a complementary determining region CDR2-VH of Y-M-N-X1-Y-N-D-G-X2-K-Y-N-X3-K-F-I-G, where X1 is A, P or G, X2 is L or I, and X3 is E, D or N;
- a complementary determining region CDR3-VH of T-X1-E-G-L-F-Y-V-X2-D-Y, where X1 is K or R, and X2 is M or F;
- a complementary determining region CDR1-VL of S-X1-T-S-S-X2-S-Y-M-H, where X1 is G or A, and X2 is I, L or V;
- a complementary determining region CDR2-VL of D-X1-S-K-L-A-S-X2-V, where X1 is T or S, and X2 is P, A or G; and

- a complementary determining region CDR3-VL of Q-X1-W-R-S-X2-L-P-T, where X1 is Q, Y or W, and X2 is D or V.

In one or more embodiments, X1 in the six CDRs of the binding protein described in the present disclosure each independently represents an amino acid defined in the present disclosure; X2 in the six CDRs of the binding protein described in the present disclosure each independently represents an amino acid defined in the present disclosure; and X3 in the six CDRs of the binding protein described in the present disclosure each independently represents an amino acid defined in the present disclosure.

It is well known in the related art that, the binding specificity and affinity of antibodies are mainly determined by CDR sequences. According to the mature and well-known existing technologies, the amino acid sequences of non-CDRs can be easily changed to obtain variants with similar activity. Accordingly, the present disclosure also includes "functional derivatives" of the binding protein. The "functional derivative" refers to a variant of an amino acid substitution. A functional derivative retains a detectable binding protein activity, such as an antibody's activity of binding to NS1 protein. The "functional derivative" may include a "variant" and a "fragment", and has similar biological activities due to the exactly same CDR sequences as the binding protein described in the present disclosure.

In one or more embodiments, the antigen-binding domain has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with the complementary determining regions of the following amino acid sequences; and the antigen-binding domain has an affinity for the NS1 protein of KD≤$5.78\times10^{-8}$ mo/L, for example, $4.45\times10^{-10}$ mol/L, $5.70\times10^{-10}$ mol/L, $6.71\times10^{-10}$ mol/L, $7.65\times10^{-10}$ mol/L, $2.85\times10^{-9}$ mol/L, $3.47\times10^{-9}$ mol/L, $4.08\times10^{-9}$ mol/L, $4.55\times10^{-9}$ mol/L, or $5.78\times10^{-8}$ mol/L; or $4.45\times10^{-10}$ mol/L≤KD≤$5.78\times10^{-8}$ mol/L, or KD smaller than or equal to $4.45\times10^{-10}$ mol/L, $5.70\times10^{-10}$ mol/L, $6.71\times10^{-10}$ mol/L, $7.65\times10^{-10}$ mol/L, $2.85\times10^{-9}$ mol/L, $3.47\times10^{-9}$ mol/L, $4.08\times10^{-9}$ mol/L, or $4.55\times10^{-9}$ mol/L.

In one or more embodiments, in the complementary determining region CDR1-VH, X1 is F; in the complementary determining region CDR2-VH, X1 is P, and X3 is E; in the complementary determining region CDR1-VL, X1 is A; in the complementary determining region CDR2-VL, X2 is G; in the complementary determining region CDR3-VL, X2 is D.

In one or more embodiments, in the complementary determining region CDR1-VH, X2 is T.

In one or more embodiments, in the complementary determining region CDR1-VH, X2 is S.

In one or more embodiments, in the complementary determining region CDR1-VH, X2 is Y.

In one or more embodiments, in the complementary determining region CDR2-VH, X2 is L.

In one or more embodiments, in the complementary determining region CDR2-VH, X2 is I.

In one or more embodiments, in the complementary determining region CDR3-VH, X1 is K, and X2 is M.

In one or more embodiments, in the complementary determining region CDR3-VH, X1 is K, and X2 is F.

In one or more embodiments, in the complementary determining region CDR3-VH, X1 is R, and X2 is M.

In one or more embodiments, in the complementary determining region CDR3-VH, X1 is R, and X2 is F.

In one or more embodiments, in the complementary determining region CDR1-VL, X2 is I.

In one or more embodiments, in the complementary determining region CDR1-VL, X2 is L.

In one or more embodiments, in the complementary determining region CDR1-VL, X2 is V.

In one or more embodiments, in the complementary determining region CDR2-VL, X1 is T.

In one or more embodiments, in the complementary determining region CDR2-VL, X1 is S.

In one or more embodiments, in the complementary determining region CDR3-VL, X1 is Q.

In one or more embodiments, in the complementary determining region CDR3-VL, X1 is Y.

In one or more embodiments, in the complementary determining region CDR3-VL, X1 is W.

In one or more embodiments, the binding protein includes at least 3 CDRs; or the binding protein includes at least 6 CDRs.

In one or more embodiments, the binding protein is a complete antibody including variable and constant regions.

In one or more embodiments, the binding protein is one of a nanobody, $F(ab')_2$, Fab', Fab, Fv, scFv, a bispecific antibody, and a minimum recognition unit of an antibody.

In one or more embodiments, the binding protein includes light chain framework regions VL-FR1, VL-FR2, VL-FR3, and VL-FR4 that have sequences set forth as SEQ ID NO: 1 to SEQ ID NO: 4, respectively, and/or heavy chain framework regions VH-FR1, VH-FR2, VH-FR3 and VH-FR4 that have sequences set forth as SEQ ID NO: 5 to SEQ ID NO: 8, respectively.

In one or more embodiments, the binding protein further includes an antibody constant region sequence.

In one or more embodiments, the constant region sequence is selected from any one of constant regions of IgG1, IgG2, IgG3, IgG4, IgA, IgM, IgE, and IgD.

In one or more embodiments, the constant region is derived from a species of cattle, horse, dairy cow, pig, sheep, goat, rat, mouse, dog, cat, rabbit, camel, donkey, deer, marten, chicken, duck, goose, turkey, cockfight, or human.

In one or more embodiments, the constant region is derived from a mouse;

a light chain constant region sequence is set forth as SEQ ID NO: 9; and a heavy chain constant region sequence is set forth as SEQ ID NO: 10.

In one or more embodiments, the present disclosure includes a nucleic acid sequence encoding the binding protein. Herein, the nucleic acid sequence includes conservatively substituted variants thereof (e.g., degenerate codon substitutions) and complementary sequences. The terms "nucleic acid" and "polynucleotide" are synonymous and encompass genes, cDNA molecules, mRNA molecules, and fragments thereof such as oligonucleotides.

In one or more embodiments, the present disclosure includes an expression vector containing a nucleic acid sequence encoding the binding protein, in which the nucleic acid sequence is operably linked to at least one regulatory sequence. The term "operably linked" means that a coding sequence is linked to a regulatory sequence in a manner that allows the expression of the coding sequence. The regulatory sequence is selected to direct the expression of the target protein in a suitable host cell, and includes promoters, enhancers and other expression control elements.

In the present disclosure, a vector may refer to a molecule or agent that contains a nucleic acid of the present disclosure or a fragment thereof and is capable of carrying genetic information and delivering the genetic information into a cell. Typical vectors include plasmids, viruses, bacteriophages, cosmids, and minichromosomes. The vector can be a cloning vector (i.e., a vector for transferring genetic information into a cell, which can be propagated and can be selected according to the presence or absence of the genetic information); or the vector can be an expression vector (i.e., the vector contains the necessary genetic elements, which allow the genetic information of the vector to be expressed in a cell). Accordingly, the cloning vector may contain a selection marker and an origin of replication that matches the cell type specified by the cloning vector; and the expression vector may contain regulatory elements necessary for affecting expression in the specified target cell.

The nucleic acids of the present disclosure or fragments thereof can be inserted into a suitable vector to form a cloning or expression vector carrying the nucleic acid fragment of the present disclosure. This new vector is also part of the present disclosure. The vector may include plasmid, bacteriophage, cosmid, minichromosome, or virus, and may further include naked DNA that is transiently expressed only in a specific cell. The cloning vector and expression vector according to the present disclosure can replicate spontaneously, and thus can provide high copy number for high-level expression or high-level replication of the subsequent cloning. The expression vector may include a promoter for driving expression of a nucleic acid fragment of the present disclosure, optionally a nucleic acid sequence encoding a signal peptide that allows the peptide expression product to be secreted onto or integrated into a membrane, a nucleic acid fragment of the present disclosure, and optionally a nucleic acid sequence encoding a terminator. When the expression vector is manipulated in a production strain or cell line, the vector can be integrated into the host cell genome when introduced into the host cell, or the vector is not integrated into the host cell genome. The vector typically carries a replication site and a marker sequence capable of providing phenotypic selection in transformed cells.

The expression vectors of the present disclosure are used to transform host cells. The transformed cells, also belonging to the present disclosure, can be cultured cells or cell lines that are used to propagate nucleic acid fragments and vectors of the present disclosure, or used to recombinantly prepare the polypeptides of the present disclosure. The transformed cells of the present disclosure include microorganisms such as bacteria (such as *E. coli, Bacillus*, etc.). The host cells include cells from multicellular organisms, for example, fungi, insect cells, plant cells, or mammalian cells such as cells from mammals, like CHO cells. The transformed cells are capable of replicating the nucleic acid fragments of the present disclosure. When the peptide combination of the present disclosure is recombinantly prepared, the expression product may be exported to a culture medium or carried on the surface of the transformed cell.

In one or more embodiments, the binding protein provided by the present disclosure can be used to detect the presence of one or more target molecules in a biological sample. The term "detection" as used herein includes quantitative or qualitative detection. In one or more embodiments, the biological sample includes cells or tissue.

As used herein, the term "colloidal gold immunoassay" is an immunolabeling technique in which colloidal gold is used as a tracer marker for antigens and/or antibodies. The colloidal gold is a stable colloidal state of gold particles having a specific size due to electrostatic action, in which the gold particles are polymerized by chloroauric acid under the action of reducing agents such as white phosphorus, ascorbic acid, sodium citrate, tannic acid, etc.

The immunoassays of the present disclosure include colloidal gold immunoassay, and further include ELISA and other assays or methods adopting antigen-antibody reactions.

In one or more embodiments, the present disclosure provides an article of manufacture (e.g., a kit) that includes a material that can be used to diagnose a dengue virus infection. The article of manufacture includes a container, and a label or package insert on or with the container. The suitable containers include, for example, bottles, or syringes, etc. The container can be made of various materials such as glass or plastic. The container is filled with a composition, which can be used to effectively diagnose dengue fever alone or in combination with another composition. At least one active agent in the composition is a binding protein provided by the present disclosure.

In one or more embodiments, the present disclosure further provides a kit including the binding protein, the nucleic acid, or the vector according to the present disclosure.

The method for detecting NS1 protein antigen in a test sample, including:

A) under conditions sufficient to cause an antibody/antigen binding reaction, forming an immune complex by contacting the NS1 protein antigen in the test sample with the binding protein as described above; and B) detecting the presence of the immune complex, the presence of the complex indicating the presence of the NS1 protein antigen in the test sample.

In one or more embodiments, the binding protein can be labeled with an indicator for displaying signal strength, thereby allowing the complex to be easily detected.

In one or more embodiments, in step A), the immune complex further includes a second antibody, and the second antibody binds to the binding protein.

In one or more embodiments, the binding protein, in a form of a first antibody, and the second antibody form paired antibodies for binding different epitopes of the NS1 protein.

The second antibody can be labeled with an indicator for displaying signal strength, thereby allowing the complex to be easily detected.

In one or more embodiments, in step A), the immune complex further includes a second antibody, and the second antibody binds to the NS1 protein antigen.

In one or more embodiments, the binding protein is used as an antigen of the second antibody, and the second antibody can be labeled with an indicator for displaying signal strength, thereby allowing the complex to be easily detected.

In one or more embodiments, the indicator for displaying signal strength includes any one of fluorescent substance, quantum dot, digoxigenin-labeled probe, biotin, radioisotope, radioactive contrast agent, paramagnetic ion fluorescent microsphere, electron dense substance, chemiluminescent label, ultrasound contrast agent, photosensitizer, colloidal gold, or enzyme.

In one or more embodiments, the fluorescent substance includes any one of: Alexa 350, Alexa 405, Alexa 430, Alexa 488, Alexa 555, Alexa 647, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxyfluorescein, 5-carboxy-2',4',5',7'-tetrachlorofluorescein, 5-carboxyfluorescein, 5-carboxyrhodamine, 6-carboxyrhodamine, 6-carboxytetramethylrhodamine, Cascade Blue, Cy2, Cy3, Cy5, Cy7, 6-FAM, dansyl chloride, fluorescein, HEX, 6-JOE, NBD (7-nitrobenzo-2-oxo-1,3-diazole), Oregon Green 488, Oregon Green 500, Oregon Green 514, Pacific Blue, phthalic acid, terephthalic acid, isophthalic acid, Cresol Fast Violet, Cresol Blue Violet, Brilliant Cresyl Blue, p-aminobenzoic acid, erythrosine, phthalocyanine, azomethine, cyanine, xanthine, succinyl fluorescein, rare earth metal cryptate, europium tribipyridyl diamine, europium cryptate or chelate, diamine, biscyanine, La Jolla blue dye, allophycocyanin, allococyanin B, phycocyanin C, phycocyanin R, thiamine, phycoerythrin, phycoerythrin R, REG, rhodamine green, rhodamine isothiocyanate, rhodamine red, ROX, TAMRA, TET, tetramethylrhodamine isothiol (TRIT), tetramethylrhodamine, and Texas Red.

In one or more embodiments, the radioisotope includes any one of $^{110}In$, $^{111}In$, $^{177}Lu$, $^{18}F$, $^{52}Fe$, $^{62}Cu$, $^{64}Cu$, $^{67}Cu$, $^{67}Ga$, $^{68}Ga$, $^{86}Y$, $^{90}Y$, $^{89}Zr$, $^{94}mTc$, $^{94}Tc$, $^{99}mTc$, $^{120}I$, $^{123}I$, $^{124}I$, $^{125}I$, $^{131}I$, $^{154-158}Gd$, $^{32}P$, $^{11}C$, $^{13}N$, $^{15}O$, $^{186}Re$, $^{188}Re$, $^{51}Mn$, $^{52}mMn$, $^{55}Co$, $^{72}As$, $^{75}Br$, $^{76}Br$, $^{82}mRb$, and $^{83}Sr$.

In one or more embodiments, the enzyme includes any one of horseradish peroxidase, alkaline phosphatase, and glucose oxidase.

In one or more embodiments, the fluorescent microsphere is polystyrene fluorescent microsphere, coated with rare earth fluorescent ion europium inside.

In one or more embodiments, the present disclosure provides a kit for determining, for example, a presence of NS1 protein in a subject infected with dengue fever, and the kit includes at least one binding protein provided by the present disclosure, related buffer, a reagent necessary for allowing a liquid sample to react with the binding protein, and a reagent for determining a presence of a positive or negative binding reaction between the NS1 protein and the binding protein. In order to determine the presence of the NS1 protein, the kit can, for example, utilize a labeled binding protein as an antibody, in which the label can be any suitable label, such as a colloidal gold label.

The present disclosure further provides a use of the binding protein according to the present disclosure for detecting a dengue infection.

The present disclosure further provides a method for detecting a dengue infection. The method includes:

A) under conditions allowing a binding reaction to occur, contacting a sample from a subject with the binding protein according to the present disclosure to perform the binding reaction; and B) detecting immune complex produced in the binding reaction, in which a presence of the immune complex indicates a presence of a dengue infection.

In one or more embodiments, the method is based on fluorescence immunoassay technology, chemiluminescence technology, immunochromatography, radioimmunoassay, and/or enzyme-linked immunoassay technology.

In one or more embodiments, the method is based on enzyme-linked immunoassay.

In one or more embodiments, the method is based on colloidal gold immunoassay.

In one or more embodiments, the sample is selected from at least one of whole blood, peripheral blood, serum, or plasma.

In one or more embodiments, the subject is a mammal, for example, a primate such as a human.

Examples provided as below are for the purpose of illustrating the present disclosure, rather than limiting the scope of the present disclosure.

Example 1

In this example, restriction enzyme and Prime Star DNA polymerase were purchased from Takara Biomedical Technology Co., Ltd. MagExtractor-RNA extraction kit was purchased from TOYOBO Co., Ltd. SMARTER™ RACE cDNA Amplification Kit was purchased from Takara Biomedical Technology Co., Ltd. The pMD-18T vector was purchased from Takara. Plasmid extraction kit was purchased from Tiangen Biotech Co., Ltd. Primer synthesis and gene sequencing were performed by Invitrogen. Hybridoma cell line secreting anti-dengue virus NS1 7F8 monoclonal antibodies was a hybridoma cell line newly selected by the Applicant.

1.1 Primer

Amplification of heavy and light chain 5'RACE primers: SMARTER II A oligonucleotide:

```
                                        (SEQ ID NO: 19)
    5'-AAGCAGTGGTATCAACGCAGAGTACXXXXX-3';
```

5'-RACE CDS primer (5'-CDS): 5'-$(T)_{25}$ VN-3' (N=A, C, G, or T; V=A, G, or C) (SEQ ID NO: 20);

```
Universal Primer A Mixture (UPM):
                                        (SEQ ID NO: 21)
5'-CTAATACGACTCACTATAGGGCAAGCAGTGGTATCAACGCAGAG

T-3';

Nested Universal Primer A (NUP):
                                        (SEQ ID NO: 22)
5'-AAGCAGTGGTATCAACGCAGAGT-3';

mkR:
                                        (SEQ ID NO: 23)
5'-CTAACACTCATTCCTGTTGAAGC-3';

mHR:
                                        (SEQ ID NO: 24)
5'-TCATTTACCAGGAGAGTGGGAGA-3.
```

1.2 Cloning and Sequencing of Antibody Variable Region Genes

RNA was extracted from hybridoma cell line secreting anti-dengue virus NS1 7F8 monoclonal antibody, and a first strand cDNA was synthesized by using SMARTER™ RACE cDNA Amplification Kit, SMARTER II A oligonucleotide in the kit, and 5'-CDS primers, and the obtained first strand cDNA product was used as a template for PCR amplification. Light chain genes were amplified with the universal primer A mixture (UPM), the nested universal primer A (NUP), and mkR primer; and heavy chain genes were amplified with the universal primer A mixture (UPM), the nested universal primer A (NUP), and mHR primer. Among them, the primer pair of light chain amplified a target band of about 0.8 KB, and the primer pair of heavy chain amplified a target band of about 1.4 KB. The product was purified and recovered by agarose gel electrophoresis, subjected to an A-tailing reaction with rTaq DNA polymerase, and then inserted into the pMD-18T vector, which was transformed into DH5a competent cells. After the growth of the bacteria, 4 clones of each of the heavy and light chain genes were taken and sent to Invitrogen for sequencing.

1.3 Sequence Analysis of the Variable Region Genes of Anti-Dengue Virus NS1 7F8 Antibodies The gene sequence obtained by the above sequencing was analyzed in the IMGT antibody database, and analysis was performed using VNTI11.5 software to confirm that the genes amplified with the heavy chain and light chain primer pair were correct, among which, in the gene fragments amplified by light chain, the VL gene sequence was 342 bp, belonging to the VkII gene family, with a 57 bp leader peptide sequence in front; and in the gene fragments amplified by the heavy chain primer pair, the VH gene sequence was 357 bp, belonging to the VIII gene family, with 57 bp leader peptide sequence in front.

1.4 Construction of Recombinant Antibody Expression Plasmid pcDNA™ 3.4 TOPO® vector was the constructed recombinant antibody eukaryotic expression vector. This expression vector had been introduced into polyclonal restriction sites such as HindIII, BamHI, EcoRI, and named as pcDNA3.4A expression vector, which is referred to as 3.4A expression vector below; according to the above pMD-18T antibody gene sequencing results, the heavy chain gene- and light chain gene-specific primers of the anti-dengue virus NS1 7F8 antibody were designed, with HindIII, EcoRI restriction sites and protective bases at both ends, the primers are as follows:

```
DN7F8-HF:
                                        (SEQ ID NO: 25)
5'-CAGAAGCTTATGAAGTTGCCTGTTAGGCTGTTGG-3';

DN7F8-HR:
                                        (SEQ ID NO: 26)
5'-CAGGAATTCTTATCATTTACCAGGAGAGTGGGAGAGGCT-3';

DN7F8-LF:
                                        (SEQ ID NO: 27)
5'-CATAAGCTTATGAAGTTGCCTGTTAGGCTGTTGGT-3';

DN7F8-LR:
                                        (SEQ ID NO: 28)
5'-ATCGAATTCTTACTAACACTCATTCCTGTTGAAGCTCTTG-3'.
```

0.75 KB light chain gene fragment and 1.42 KB heavy chain gene fragment were amplified by PCR amplification method. The heavy and light chain gene fragments were double-enzyme digested with HindIII/EcoRI, and the 3.4A vector was double-enzyme digested with HindIII/EcoRI. After the fragment and the vector were purified and recovered, the heavy chain and light chain genes were ligated into the 3.4A expression vectors, respectively, so as to obtain recombinant expression plasmids for heavy and light chains, respectively.

Example 2

1. Identification of Expression Supernatant Binding Protein Activity

The plasmid was diluted to 400 ng/ml with ultrapure water, and in a centrifuge tube, the Chinese hamster ovary CHO cells were adjusted to 1.43×107 cells/mL. 100 µl of the plasmid and 700 µl of the cells were mixed, transferred to an electro-revolving cup for electric revolving, then transferred to 10 ml of medium containing CD CHO AGT, and cultured in a shaker at 37° C. (8% $CO_2$, shaking amplitude of 150); sample was taken to detect the cell viability every day, and when the cell viability was lower than 50%, the cell culture supernatant was centrifuged to obtain a protein sample.

Antigen DN-IV-Ag #(Fapon Biotech Inc.) was diluted 1000 times with CB, 100 µl of polystyrene enzyme standard block was added to each well, and overnight at 4° C.; on the next day, washed with the washing solution PBST, patted dry; added with blocking buffer (20% BSA+80% PBS), 120 µl per well, at 37° C., after 1 h, patted dry; added with the diluted cell supernatant, 100 µl/well, at 37° C., for 30 min (partial supernatant 1 h); washed with wash solution 5 times, patted dry; added with sheep anti-mouse IgG-HRP, 100 µl/well, 37° C., 30 min; washed with the washing solution 5 times, patted dry; added with solution A of chromogenic solution (50 µl/well), added with solution B of chromogenic solution (50 µl/well), for 10 min; added with a blocking buffer, 50 µl/well; and the OD values were read on microplate reader at 450 nm (reference, 630 nm).

2. Purification of Binding Protein

The above sample was subjected to affinity purification using a protein A affinity chromatography column, and 500 mg of recombinant antibody was obtained after the purification, and 4 µg of the purified antibody was subjected to reduced SDS-PAGE. Two bands were shown after the reduced SDS-PAGE, one of which was a 28KD light chain (sequence set forth as SEQ ID NO: 11), and the other one of which was a 50KD heavy chain (sequence set forth as SEQ ID NO: 12).

3. Antibody Affinity Analysis

With an AMC sensor, the purified antibody was diluted to 10 µg/ml with PBST, and DN-IV quality control recombinant protein (produced by the company) was gradient diluted with PBST to 500 nmol/ml, 250 nmol/ml, 125 nmol/ml, 62.5 nmol/ml, 31.3 nmol/ml, 15.6 nmol/ml, 7.81 nmol/ml, and 0 nmol/ml.

Operating procedure: equilibrating for 60 s in Buffer 1 (PBST), solidifying the antibody for 300 s in the antibody solution, incubating for 180 s in Buffer 2 (PBST), binding for 420 s in the antigen solution, dissociating for 1200 s in Buffer 2, and using 10 mM of GLY solution (pH 1.69) and Buffer 3 to perform sensor regeneration, and outputting data. (KD represents an equilibrium dissociation constant, which is a measure for affinity; kon represents a binding rate; and koff represents a dissociation rate), and the data is output.

Example 3

Although the antibody obtained in Example 2 (having the light and heavy chains set forth as SEQ ID NOs: 11 and 12) had the ability to bind to the NS1 protein, the affinity and antibody activity thereof were not ideal. Therefore, Applicant performed mutations on the light chain CDR and the heavy chain CDR of the antibody.

Through analysis, the complementary determining regions of the heavy chain:

CDR1-VH is G-Y-T-V (X1)-T-S-T (X2)-V-I-H;

CDR2-VH is Y-M-N-A (X1)-Y-N-D-G-L (X2)-K-Y-N-D (X3)-K-F-I-G;

CDR3-VH is T-K (X1)-E-G-L-F-Y-V-M (X2)-D-Y;

the complementary determining regions of the light chain:

CDR1-VL is S-G (X1)-T-S-S-I (X2)-S-Y-M-H;

CDR2-VL is D-T (X1)-S-K-L-A-S-P (X2)-V;

CDR3-VL is Q-Q (X1)-W-R-S-V (X2)-L-P-T.

Among them, X1, X2, and X3 are mutation sites.

After the mutation, the method provided in Example 2 was used to detect the antibody activity, and some of the results were as follows:

TABLE 1

Mutation sites related to antibody activity

| Site | CDR-VH1 X1 | CDR-VH2 X1/X3 | CDR-VL1 X1 | CDR-VL2 X2 | CDR-VL3 X2 |
|---|---|---|---|---|---|
| WT | V | A/D | G | P | V |
| Mutation 1 | F | P/E | A | G | D |
| Mutation 2 | F | G/N | A | A | D |
| Mutation 3 | L | K/P | V | C | Q |
| Mutation 4 | R | E/L | I | W | Y |
| Mutation 5 | C | R/F | P | R | T |

TABLE 2

Analysis of antibody activity

| | WT | Mutation 1 | Mutation 2 | Mutation 3 | Mutation 4 | Mutation 5 |
|---|---|---|---|---|---|---|
| Initial | 1.419 | 1.611 | 1.595 | 0.923 | 0.721 | — |
| Diluted 3 times | 1.183 | 1.394 | 1.475 | 0.347 | 0.056 | — |
| Diluted 9 times | 0.781 | 1.073 | 1.055 | 0.062 | — | — |
| Diluted 27 times | 0.398 | 0.445 | 0.578 | — | — | — |
| Diluted 81 times | 0.240 | 0.203 | 0.216 | — | — | — |
| Diluted 243 times | 0.200 | 0.103 | 0.110 | — | — | — |
| Diluted 729 times | 0.211 | 0.111 | 0.157 | | | |
| Blank | 0.232 | 0.125 | 0.022 | — | — | — |

"—" represents inactive

As reflected in the above table, Mutation 1 has the best effect on activity, and thus Mutation 1 was used as a framework sequence to screen mutation sites with better potency. Some of the results are shown as follows.

TABLE 3

| Mutation sites related to antibody affinity | | | | | | |
|---|---|---|---|---|---|---|
| Site | CDR-VH1 X2 | CDR-VH2 X2 | CDR-VH3 X1/X2 | CDR-VL1 X2 | CDR-VL2 X1 | CDR-VL3 X1 |
| Mutation 1 | T | L | K/M | I | T | Q |
| Mutation 1-1 | S | I | K/F | L | S | W |
| Mutation 1-2 | Y | L | R/M | V | T | Q |
| Mutation 1-3 | T | I | R/F | I | S | Y |
| Mutation 1-4 | S | L | K/M | L | T | W |
| Mutation 1-5 | Y | I | R/F | V | S | Q |
| Mutation 1-6 | T | I | K/M | I | T | Y |
| Mutation 1-7 | S | L | K/F | L | S | W |
| Mutation 1-8 | Y | I | R/M | V | T | Q |
| Mutation 1-9 | T | L | R/F | I | S | Y |
| Mutation 1-10 | S | I | K/M | L | T | W |
| Mutation 1-11 | Y | L | K/F | V | S | Q |
| Mutation 1-12 | T | I | R/M | I | T | Y |
| Mutation 1-13 | S | L | R/F | L | S | W |
| Mutation 1-14 | Y | I | K/M | V | S | Q |
| Mutation 1-15 | T | I | K/F | I | S | Y |
| Mutation 1-16 | S | L | R/M | L | T | W |
| Mutation 1-17 | Y | I | K/M | V | S | W |
| Mutation 1-18 | T | L | K/F | L | S | Y |
| Mutation 1-19 | S | I | R/M | V | T | Q |
| Mutation 1-20 | Y | L | K/F | I | S | Y |
| Mutation 1-21 | T | I | R/M | L | T | W |
| Mutation 1-22 | S | L | R/F | V | S | W |
| Mutation 1-23 | Y | L | K/F | L | S | Q |
| Mutation 1-24 | T | I | R/M | V | T | Y |
| Mutation 1-25 | S | L | R/F | I | S | W |
| Mutation 1-26 | Y | I | R/M | L | T | W |
| Mutation 1-27 | T | L | R/F | V | S | Q |
| Mutation 1-28 | S | I | K/M | V | T | Y |
| Mutation 1-29 | Y | I | R/F | I | S | W |
| Mutation 1-30 | T | L | R/M | L | T | Y |
| Mutation 1-31 | S | I | R/F | V | S | W |
| Mutation 1-32 | Y | I | K/M | V | T | Q |
| Mutation 1-33 | T | L | R/F | I | S | W |
| Mutation 1-34 | S | I | R/F | L | T | Y |
| Mutation 1-35 | Y | L | K/M | V | S | W |
| Mutation 1-36 | T | L | R/F | L | S | Q |
| Mutation 1-37 | S | I | R/F | V | T | Y |
| Mutation 1-38 | Y | L | K/M | I | S | W |
| Mutation 1-39 | T | I | R/F | L | S | Q |
| Mutation 1-40 | S | L | K/F | V | T | Y |
| Mutation 1-41 | Y | I | R/M | I | S | W |
| Mutation 1-42 | T | I | R/F | L | T | Q |
| Mutation 1-43 | S | I | K/M | L | T | Y |
| Mutation 1-44 | Y | L | R/F | V | S | Y |
| Mutation 1-45 | T | I | K/F | L | S | W |
| Mutation 1-46 | S | L | R/M | V | T | Q |
| Mutation 1-47 | Y | I | R/F | I | S | Y |
| Mutation 1-48 | T | L | K/M | L | S | W |
| Mutation 1-49 | S | I | R/F | V | T | Q |
| Mutation 1-50 | Y | L | K/F | I | T | Y |
| Mutation 1-51 | T | L | R/M | I | S | W |
| Mutation 1-52 | S | L | K/F | L | S | Q |
| Mutation 1-53 | Y | I | R/M | V | T | Y |

TABLE 4

| Affinity analysis data | | | |
|---|---|---|---|
| | KD (M) | Kon (1/Ms) | Koff (VS) |
| Mutation 1 | 2.85E−09 | 4.42E+04 | 1.26E−04 |
| Mutation 1-1 | 4.45E−10 | 4.07E+05 | 1.81E−04 |
| Mutation 1-2 | 2.79E−09 | 4.16E+04 | 1.16E−04 |
| Mutation 1-3 | 2.90E−09 | 4.11E+04 | 1.19E−04 |
| Mutation 1-4 | 4.78E−10 | 4.90E+05 | 2.34E−04 |
| Mutation 1-5 | 5.08E−10 | 4.19E+05 | 2.13E−04 |
| Mutation 1-6 | 4.99E−10 | 4.99E+05 | 2.49E−04 |
| Mutation 1-7 | 6.52E−10 | 3.68E+05 | 2.40E−04 |
| Mutation 1-8 | 4.08E−09 | 4.22E+04 | 1.72E−04 |
| Mutation 1-9 | 6.60E−10 | 4.30E+05 | 2.84E−04 |
| Mutation 1-10 | 2.65E−09 | 4.87E+04 | 1.29E−04 |
| Mutation 1-11 | 7.25E−10 | 4.14E+05 | 3.00E−04 |
| Mutation 1-12 | 2.86E−09 | 4.26E+04 | 1.22E−04 |
| Mutation 1-13 | 3.47E−09 | 4.35E+04 | 1.51E−04 |
| Mutation 1-14 | 2.75E−09 | 4.36E+04 | 1.20E−04 |
| Mutation 1-15 | 3.79E−09 | 4.48E+04 | 1.70E−04 |
| Mutation 1-16 | 3.38E−09 | 3.67E+04 | 1.24E−04 |
| Mutation 1-17 | 2.52E−09 | 4.52E+04 | 1.14E−04 |
| Mutation 1-18 | 5.72E−10 | 4.25E+05 | 2.43E−04 |
| Mutation 1-19 | 2.41E−09 | 4.68E+04 | 1.13E−04 |
| Mutation 1-20 | 3.53E−09 | 4.56E+04 | 1.61E−04 |
| Mutation 1-21 | 6.93E−10 | 3.88E+05 | 2.69E−04 |
| Mutation 1-22 | 5.90E−10 | 4.15E+05 | 2.45E−04 |
| Mutation 1-23 | 3.97E−09 | 4.78E+04 | 1.90E−04 |
| Mutation 1-24 | 2.85E−09 | 4.66E+04 | 1.33E−04 |
| Mutation 1-25 | 2.92E−09 | 4.79E+04 | 1.40E−04 |
| Mutation 1-26 | 3.61E−09 | 4.21E+04 | 1.52E−04 |
| Mutation 1-27 | 3.55E−09 | 4.20E+04 | 1.49E−04 |
| Mutation 1-28 | 5.91E−10 | 4.38E+05 | 2.59E−04 |
| Mutation 1-29 | 4.93E−10 | 3.61E+05 | 1.78E−04 |
| Mutation 1-30 | 3.12E−09 | 4.23E+04 | 1.32E−04 |
| Mutation 1-31 | 5.79E−10 | 3.97E+05 | 2.30E−04 |
| Mutation 1-32 | 6.31E−10 | 3.50E+05 | 2.21E−04 |
| Mutation 1-33 | 5.60E−10 | 4.93E+05 | 2.76E−04 |
| Mutation 1-34 | 2.89E−09 | 3.87E+04 | 1.12E−04 |
| Mutation 1-35 | 6.61E−10 | 3.81E+05 | 2.52E−04 |
| Mutation 1-36 | 6.57E−10 | 4.29E+05 | 2.82E−04 |
| Mutation 1-37 | 3.63E−09 | 3.99E+04 | 1.45E−04 |
| Mutation 1-38 | 6.43E−10 | 4.54E+05 | 2.92E−04 |
| Mutation 1-39 | 4.55E−09 | 4.09E+04 | 1.86E−04 |
| Mutation 1-40 | 6.71E−10 | 3.89E+05 | 2.61E−04 |
| Mutation 1-41 | 4.55E−10 | 3.52E+05 | 1.60E−04 |
| Mutation 1-42 | 5.32E−10 | 3.93E+05 | 2.09E−04 |
| Mutation 1-43 | 6.24E−10 | 4.10E+05 | 2.56E−04 |
| Mutation 1-44 | 2.63E−09 | 4.18E+04 | 1.10E−04 |
| Mutation 1-45 | 4.22E−09 | 4.12E+04 | 1.74E−04 |
| Mutation 1-46 | 5.69E−10 | 3.90E+05 | 2.22E−04 |
| Mutation 1-47 | 5.70E−10 | 3.70E+05 | 2.11E−04 |
| Mutation 1-48 | 6.65E−10 | 3.73E+05 | 2.48E−04 |
| Mutation 1-49 | 7.65E−10 | 3.91E+05 | 2.99E−04 |
| Mutation 1-50 | 3.79E−09 | 4.41E+04 | 1.67E−04 |
| Mutation 1-51 | 5.00E−10 | 4.02E+05 | 2.01E−04 |
| Mutation 1-52 | 3.02E−09 | 4.10E+04 | 1.24E−04 |
| Mutation 1-53 | 2.71E−09 | 4.25E+04 | 1.15E−04 |

The above experiment was repeated using WT as the framework sequence to verify the affinity of the mutation site. Some of the results are shown as follows.

TABLE 5

| Mutations using WT as framework | | | | | | |
|---|---|---|---|---|---|---|
| Site | CDR-VH1 X2 | CDR-VH2 X2 | CDR-VH3 X1/X2 | CDR-VL1 X2 | CDR-VL2 X1 | CDR-VL3 X1 |
| WT | S | I | K/M | L | T | Q |
| WT 1-5 | Y | L | K/F | V | S | W |
| WT 1-11 | T | I | R/M | I | T | Y |
| WT 1-14 | S | L | R/F | L | S | W |
| WT 1-19 | Y | I | K/M | V | S | Q |

TABLE 6

| Affinity analysis data | | | |
|---|---|---|---|
| | KD (M) | Kon (1/Ms) | Koff (VS) |
| WT | 3.15E−09 | 4.42E+04 | 1.39E−04 |
| WT 1-5 | 5.78E−08 | 4.57E+03 | 2.64E−04 |
| WT 1-11 | 5.71E−08 | 4.27E+03 | 2.44E−04 |
| WT 1-14 | 4.56E−08 | 4.12E+03 | 1.88E−04 |
| WT 1-19 | 3.54E−08 | 4.57E+03 | 1.62E−04 |

Based on the analysis data in the above tables, on the premise of ensuring antibody activity, the affinity of all the antibodies based on the framework of Mutation 1 is higher than that of antibody using WT as the framework.

Example 4

The above self-produced antibodies were placed at 4° C. (refrigerator), −80° C. (refrigerator), 37° C. (incubator) for 21 days, and samples of 7 days, 14 days, and 21 days were taken for state observation, and the samples of 21 days were tested for activity, and the results reveal that, under the three assessment conditions, no significant changes of protein status were observed after the antibodies were placed for 21 days, and the activity did not decrease with the rise of the assessment temperature, indicating that the self-produced antibodies were stable. The following table shows OD results of enzyme immunoassay for 21 days.

TABLE 7

| Assessment of antibody stability | | | |
|---|---|---|---|
| Sample concentration (μg/ml) | 3 | 0.75 | 0 |
| 4° C., sample of 21 days | 2.433 | 0.876 | 0.004 |
| −80° C., sample of 21 days | 2.345 | 0.854 | 0.006 |
| 37° C., sample of 21 days | 2.476 | 0.836 | 0.009 |

It should be noted that the above embodiments are only used to illustrate the technical solutions of the present disclosure, rather than limiting them. Although the present disclosure has been described in detail with reference to the foregoing examples, those skilled in the art should understand that they can modify the technical solutions described in the foregoing embodiments, or replace some or all of the technical features equivalently; and these modifications or replacements do not deviate the essence of the corresponding technical solutions from the scope of the technical solutions of the embodiments of the present disclosure.

INDUSTRIAL APPLICABILITY

In the present disclosure, the isolated binding protein including an antigen-binding domain that binds to NS1 protein, includes specific heavy chain CDRs and light chain CDRs. The binding protein can specifically recognize and bind to NS1, and has relatively high sensitivity and specificity, thereby achieving the detection of dengue virus. In addition, the binding protein is not required to be produced by inducing hybridoma cells in mouse abdominal cavity, and thus it is simple in production and has more stable antibody function.

What is claimed is:

1. An isolated binding protein of dengue virus NS1 protein, the binding protein comprising a light chain and a heavy chain, wherein an antigen-binding domain of the heavy chain comprises:

a complementary determining region CDR1-VH of G-Y-T-X1-T-S-X2-V-I-H as set forth in SEQ ID NO: 13 wherein the complementary determining region CDR1-VH corresponds to the amino acid sequence at position 26 to 35 on the heavy chain according to the Kabat numbering system;

a complementary determining region CDR2-VH of Y-M-N-X1-Y-N-D-G-X2-K-Y-N-X3-K-F-I-G as set forth in SEQ ID NO: 14 wherein the complementary determining region CDR2-VH corresponds to the amino acid sequence at position 50 to 65 on the heavy chain according to the Kabat numbering system;

a complementary determining region CDR3-VH of T-X1-E-G-L-F-Y-V-X2-D-Y as set forth in SEQ ID NO: 15 wherein the complementary determining region CDR3-VH corresponds to the amino acid sequence at position 93 to 102 on the heavy chain according to the Kabat numbering system, wherein an antigen-binding domain of the heavy chain comprises:

a complementary determining region CDR1-VL of S-X1-T-S-S-X2-S-Y-M-H as set forth in SEQ ID NO: 16 wherein the complementary determining region CDR1-VL corresponds to the amino acid sequence at position 24 to 34 on the light chain according to the Kabat numbering system;

a complementary determining region CDR2-VL of D-X1-S-K-L-A-S-X2-V as set forth in SEQ ID NO: 17 wherein the complementary determining region CDR2-VL corresponds to the amino acid sequence at position 50 to 58 on the light chain according to the Kabat numbering system; and a complementary determining region CDR3-VL of Q-X1-W-R-S-X2-L-P-T as set forth in SEQ ID NO: 18 wherein the complementary determining region CDR3-VL corresponds to the amino acid sequence at position 89 to 97 on the light chain according to the Kabat numbering system, wherein an amino acid at a corresponding site of the complementary determining regions is as follows:

| Site | CDR1-VH X2 | CDR2-VH X2 | CDR3-VH X1/X2 | CDR1-VL X2 | CDR2-VL X1 | CDR3-VL X1 |
|---|---|---|---|---|---|---|
| Mutation 1 | T | L | K/M | I | T | Q |
| Mutation 1-1 | S | I | K/F | L | S | W |
| Mutation 1-2 | Y | L | R/M | V | T | Q |
| Mutation 1-3 | T | I | R/F | I | S | Y |

-continued

| Site | CDR1-VH X2 | CDR2-VH X2 | CDR3-VH X1/X2 | CDR1-VL X2 | CDR2-VL X1 | CDR3-VL X1 |
|---|---|---|---|---|---|---|
| Mutation 1-4 | S | L | K/M | L | T | W |
| Mutation 1-5 | Y | I | R/F | V | S | Q |
| Mutation 1-6 | T | I | K/M | I | T | Y |
| Mutation 1-7 | S | L | K/F | L | S | W |
| Mutation 1-8 | Y | I | R/M | V | T | Q |
| Mutation 1-9 | T | L | R/F | I | S | Y |
| Mutation 1-10 | S | I | K/M | L | T | W |
| Mutation 1-11 | Y | L | K/F | V | S | Q |
| Mutation 1-12 | T | I | R/M | I | T | Y |
| Mutation 1-13 | S | L | R/F | L | S | W |
| Mutation 1-14 | Y | I | K/M | V | S | Q |
| Mutation 1-15 | T | I | K/F | I | S | Y |
| Mutation 1-16 | S | L | R/M | L | T | W |
| Mutation 1-17 | Y | I | K/M | V | S | W |
| Mutation 1-18 | T | L | K/F | L | S | Y |
| Mutation 1-19 | S | I | R/M | V | T | Q |
| Mutation 1-20 | Y | L | K/F | I | S | Y |
| Mutation 1-21 | T | I | R/M | L | T | W |
| Mutation 1-22 | S | L | R/F | V | S | W |
| Mutation 1-23 | Y | L | K/F | L | S | Q |
| Mutation 1-24 | T | I | R/M | V | T | Y |
| Mutation 1-25 | S | L | R/F | I | S | W |
| Mutation 1-26 | Y | I | R/M | L | T | W |
| Mutation 1-27 | T | L | R/F | V | S | Q |
| Mutation 1-28 | S | I | K/M | V | T | Y |
| Mutation 1-29 | Y | I | R/F | I | S | W |
| Mutation 1-30 | T | L | R/M | L | T | Y |
| Mutation 1-31 | S | I | R/F | V | S | W |
| Mutation 1-32 | Y | I | K/M | V | T | Q |
| Mutation 1-33 | T | L | R/F | I | S | W |
| Mutation 1-34 | S | I | R/F | L | T | Y |

-continued

| Site | CDR1-VH X2 | CDR2-VH X2 | CDR3-VH X1/X2 | CDR1-VL X2 | CDR2-VL X1 | CDR3-VL X1 |
|---|---|---|---|---|---|---|
| Mutation 1-35 | Y | L | K/M | V | S | W |
| Mutation 1-36 | T | L | R/F | L | S | Q |
| Mutation 1-37 | S | I | R/F | V | T | Y |
| Mutation 1-38 | Y | L | K/M | I | S | W |
| Mutation 1-39 | T | I | R/F | L | S | Q |
| Mutation 1-40 | S | L | K/F | V | T | Y |
| Mutation 1-41 | Y | I | R/M | I | S | W |
| Mutation 1-42 | T | I | R/F | L | T | Q |
| Mutation 1-43 | S | I | K/M | L | T | Y |
| Mutation 1-44 | Y | L | R/F | V | S | Y |
| Mutation 1-45 | T | I | K/F | L | S | W |
| Mutation 1-46 | S | L | R/M | V | T | Q |
| Mutation 1-47 | Y | I | R/F | I | S | Y |
| Mutation 1-48 | T | L | K/M | L | S | W |
| Mutation 1-49 | S | I | R/F | V | T | Q |
| Mutation 1-50 | Y | L | K/F | I | T | Y |
| Mutation 1-51 | T | L | R/M | I | S | W |
| Mutation 1-52 | S | L | K/F | L | S | Q |
| Mutation 1-53 | Y | I | R/M | V | T | Y. |

2. The binding protein according to claim 1, wherein the binding protein further comprises an antibody constant region sequence.

3. A nucleic acid encoding the binding protein according to claim 1.

4. A vector, comprising a nucleic acid encoding the binding protein according to claim 1.

5. An isolated host cell, comprising a nucleic acid encoding the binding protein according to claim 1 or a vector comprising the nucleic acid.

6. A kit, comprising the binding protein according to claim 1.

7. A method for producing the binding protein according to claim 1, the method comprising:

culturing isolated host cells in a medium, and collecting the produced binding protein from the medium or from the cultured host cells, wherein the isolated host cells comprise a nucleic acid encoding the binding protein, or a vector comprising the nucleic acid encoding the binding protein.

8. A device for detecting a dengue infection, wherein the device comprises the binding protein according to claim 1.

9. A method for detecting dengue virus NS1 protein antigen in a test sample, comprising:

A) under conditions allowing an antibody-antigen binding reaction to occur, forming an immune complex by contacting the NS1 protein antigen in the test sample with the binding protein according to claim 1; and B) detecting a presence of the immune complex, the presence of the complex indicating a presence of the NS1 protein antigen in the test sample.

10. The method according to claim 9, wherein the method is based on fluorescence immunoassay technology, chemiluminescence technology, colloidal gold immunoassay technology, radioimmunoassay, and/or enzyme-linked immunoassay technology.

11. The binding protein according to claim 1, wherein the binding protein is labelled with an indicator for displaying signal strength.

12. The binding protein according to claim 1, wherein the binding protein is one of $F(ab')_2$, Fab', Fab, Fv, scFv, and bispecific antibody.

13. The binding protein according to claim 1, wherein the binding protein comprises light chain framework regions VL-FR1, VL-FR2, VL-FR3, and VL-FR4 that have sequences set forth as SEQ ID NO: 1 to SEQ ID NO: 4, respectively, and/or heavy chain framework regions VH-FR1, VH-FR2, VH-FR3 and VH-FR4 that have sequences set forth as SEQ ID NO: 5 to SEQ ID NO: 8, respectively.

14. The binding protein according to claim 2, wherein the constant region sequence is a sequence of constant region selected from any one of IgG1, IgG2, IgG3, IgG4, IgA, IgM, IgE, and IgD.

15. The binding protein according to claim 2, wherein the constant region is derived from a species of cattle, horse, pig, sheep, goat, rat, mouse, dog, cat, rabbit, camel, donkey, deer, marten, chicken, duck, goose, or human.

16. The binding protein according to claim 2, wherein the constant region is derived from a mouse; a light chain constant region sequence is set forth as SEQ ID NO: 9; and a heavy chain constant region sequence is set forth as SEQ ID NO: 10.

17. The method according to claim 9, wherein the test sample is selected from at least one of whole blood, peripheral blood, serum, or plasma.

* * * * *